US012642217B2

(12) United States Patent
Brinkman et al.

(10) Patent No.: US 12,642,217 B2
(45) Date of Patent: *Jun. 2, 2026

(54) PLANTS AND SEEDS OF HYBRID CORN VARIETY CH010482

(71) Applicant: Monsanto Technology LLC, St. Louis, MO (US)

(72) Inventors: Mark J. Brinkman, Omaha, NE (US); Judd J. Maxwell, Sycamore, IL (US); Laron L. Peters, Gothenburg, NE (US); Scott C. Stelpflug, Ankeny, IA (US)

(73) Assignee: Monsanto Technology LLC, St. Louis, MO (US)

( * ) Notice: Subject to any disclaimer, the term of this patent is extended or adjusted under 35 U.S.C. 154(b) by 193 days.

This patent is subject to a terminal disclaimer.

(21) Appl. No.: 18/391,883

(22) Filed: Dec. 21, 2023

(65) Prior Publication Data

US 2025/0204401 A1      Jun. 26, 2025

(51) Int. Cl.
*A01H 6/46*      (2018.01)
*A01H 5/10*      (2018.01)

(52) U.S. Cl.
CPC ............. *A01H 6/4684* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 4,658,085 A | 4/1987 | Beversdorf et al. |
| 5,523,520 A | 6/1996 | Hunsperger et al. |
| 5,773,683 A | 6/1998 | Foley |
| 6,433,261 B2 | 8/2002 | Hotchkiss |
| 6,693,232 B1 | 2/2004 | Bergemann |
| 6,852,915 B2 | 2/2005 | Johnson |

| | | | |
|---|---|---|---|
| 11,259,486 B1 * | 3/2022 | Boerboom ........... | A01H 6/4684 |
| 2025/0204392 A1 | 6/2025 | Brinkman et al. | |
| 2025/0204393 A1 | 6/2025 | Brinkman et al. | |

OTHER PUBLICATIONS

Eshed et al., "Less-Than-Addictive Epistatic Interactions of Quantitative Trait Loci in Tomato," Genetics, 143:1807-1817, 1996.
Fehr (ed), "Backcross Method," In: Principles of Cultivar Development, vol. 1: Theory and Technique, pp. 360-376, 1987.
Hallauer et al., "Corn Breeding," In: Corn and Corn Improvement, Sprague et al. (Eds.), Madison, Wisconsin, Ch. 8, pp. 463-564, 1988.
Kraft et al.,"Linkage Disequilibrium and Fingerprinting in Sugar Beet," Theor Appl Genet, 101:323-326, 2000.
Krakowsky et al., "Quantitative, Trait loci for Cell Wall Components in Recombinant Inbred Lines of Maize (*Zea mays* L.) II: Leaf sheath Tissue," Theor Appl Genet 112:717-726, 2006.
Larson et al., "Corn Production," In: Corn and Corn Improvement, G.F. Sprague (Ed.), No. 18 in Agronomy Series, American Society Agronomy, Inc., Madison, Wisconsin, pp. 625-669, 1977.
Meghji et al., "Inbreeding Depression, Inbred and Hybrid Grain Yields, and Other Traits of Maize Genotypes Representing Three Eras," Crop Science, 24:545-549, 1984.
Sprague et al., "Corn Breeding," In: Corn and Corn Improvement, G.F. Sprague (Ed.), No. 18 in Agronomy Series, American Society Agronomy, Inc., Madison, Wisconsin, pp. 305-362, 1977.
Wych, Production of Hybrid Seed Corn, In: Corn and Corn Improvement, Sprague et al. (Eds.), Madison, Wisconsin, Ch. 9, pp. 565-607, 1988.
Variety specific information as indicated in Transmittal Letter for U.S. Appl. No. 18/391,883, dated Jul. 21, 2025.

* cited by examiner

*Primary Examiner* — Weihua Fan
(74) *Attorney, Agent, or Firm* — Paul D. Tietz; Ann H. Inglett; Gale Wesley Starkey

(57) ABSTRACT

According to the disclosure, there is provided seed and plants of the hybrid corn variety designated CH010482. The disclosure thus relates to the plants, seeds, and tissue cultures of the variety CH010482, and to methods for producing a corn plant produced by crossing a corn plant of variety CH010482 with itself or with another corn plant, such as a plant of another variety. The disclosure further relates to genetic complements of plants of variety CH010482.

17 Claims, No Drawings

PLANTS AND SEEDS OF HYBRID CORN VARIETY CH010482

BACKGROUND

Field

The present disclosure relates to the field of corn breeding. In particular, the disclosure relates to corn seed and plants of the hybrid variety designated CH010482, and derivatives and tissue cultures thereof.

Description of Related Art

The goal of field crop breeding is to combine various desirable traits in a single variety/hybrid. Such desirable traits include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Plant breeding techniques take advantage of how a plant is naturally pollinated. There are two general methods of pollination. A plant is self-pollinated when pollen from one flower is transferred to the same flower or another flower of the same plant. A plant is cross-pollinated when pollen comes to it from a flower of a different plant.

Corn plants (*Zea mays* L.) can be bred by both self-pollination and cross-pollination. Both types of pollination involve the corn plant's flowers. Corn has separate male and female flowers on the same plant, which are located on the tassel and the ear, respectively. Natural pollination occurs in corn when the wind blows pollen from the tassels to the silks that protrude from the tops of the ear shoot.

Plants that have been self-pollinated and selected for type over many generations become homozygous at almost all gene loci and produce a uniform population of true breeding progeny, i.e., a homozygous plant. A cross between two such homozygous plants produces a uniform population of hybrid plants that are heterozygous for many gene loci and phenotypically uniform.

The development of uniform corn plant hybrids requires developing homozygous inbred plants, crossing these inbred plants, and evaluating these crosses. Pedigree breeding and recurrent selection are examples of breeding methods used to develop hybrid parent plants from breeding populations. Those breeding methods combine the genetic backgrounds from two or more inbred plants or various other broad-based sources into breeding pools from which new inbred plants are developed by selfing combined with phenotypic or genotypic selection. The new inbred plants are crossed with other inbred plants and the hybrids produced by these crosses are evaluated for commercial potential.

North American farmers plant tens of millions of acres of corn at the present time and there are extensive national and international commercial corn breeding programs. A continuing goal of these corn breeding programs is to develop corn hybrids that are based on stable inbred plants and have one or more desirable characteristics. To accomplish this goal, the corn breeder must select and develop superior inbred parental plants.

SUMMARY

In one aspect, the present disclosure provides a corn plant of the hybrid variety designated CH010482. Also provided are corn plants having all the physiological and morphological characteristics of the hybrid corn variety CH010482. A hybrid corn plant disclosed herein may further comprise a cytoplasmic or nuclear factor that may confer male sterility or otherwise preventing self-pollination, such as by self-incompatibility. Parts of the corn plant of the present disclosure are also provided, for example, pollen obtained from a hybrid plant and an ovule of the hybrid plant. The disclosure also concerns seed of the hybrid corn variety CH010482. The hybrid corn seed disclosed herein may be provided as a population of corn seed of the variety designated CH010482.

In a further aspect, the disclosure provides a composition comprising a seed of corn variety CH010482 comprised in plant seed growth media. In certain embodiments, the plant seed growth media is a soil or synthetic cultivation medium. In specific embodiments, the growth medium may be comprised in a container or may, for example, be soil in a field.

In another aspect, the hybrid corn variety CH010482 comprising an added heritable trait or genetic modification is provided. The heritable trait may comprise a genetic locus that comprises a dominant or recessive allele. In certain embodiments, the genetic locus confers traits such as, for example, male sterility, waxy starch, herbicide resistance, insect resistance, resistance to bacterial, fungal, nematode, or viral disease, and altered fatty acid, phytate or carbohydrate metabolism. In certain embodiments, the genetic locus that confers herbicide resistance may confer resistance to herbicides such as, for example, imidazolinone herbicides, sulfonylurea herbicides, triazine herbicides, phenoxy herbicides, cyclohexanedione herbicides, benzonitrile herbicides, 4-hydroxyphenylpyruvate dioxygenase-inhibiting herbicides, protoporphyrinogen oxidase-inhibiting herbicides, acetolactate synthase-inhibiting herbicides, 1-aminocyclopropane-1-carboxylic acid synthase-inhibiting herbicides, bromoxynil, nicosulfuron, 2,4-dichlorophenoxyacetic acid (2,4-D), dicamba, quizalofop-p-ethyl, glyphosate, or glufosinate. The genetic locus may be a naturally occurring corn gene introduced into the genome of a parent of the variety by backcrossing, a natural or induced mutation, or a transgene introduced through genetic transformation techniques. When introduced through transformation, a genetic locus may comprise one or more transgenes integrated at a single chromosomal location.

In further embodiments, a single locus conversion of one or both parental varieties of the hybrid corn variety CH010482 comprises a heritable genetic modification to the genome of one or both parental varieties. A heritable genetic modification may comprise, for example, an insertion, deletion, or substitution of a nucleotide sequence. In certain embodiments, a single locus may comprise one or more genes or intergenic regions integrated into or mutated at a single locus or may comprise one or more nucleic acid molecules integrated at the single locus. In particular embodiments, a single locus conversion may be generated by genome editing such as through use of engineered nucleases, as is known in the art. Examples of engineered nucleases include, but are not limited to, Cas endonucleases, zinc finger nucleases (ZFNs), transcription activator-like effector nucleases (TALENs), and engineered meganucleases, also known as homing endonucleases. Naturally occurring nucleases can also find use for genome editing. In specific embodiments, endonucleases, both naturally occurring and engineered, may utilize any polypeptide-, DNA-, or RNA-guided genome editing systems known to the skilled artisan.

In yet another aspect, a hybrid corn plant of the variety designated CH010482 is provided, wherein a cytoplasmi-cally-inherited trait has been introduced into said hybrid plant. Such cytoplasmically inherited traits are passed to progeny through the female parent in a particular cross. An exemplary cytoplasmically-inherited trait is the male steril-ity trait. Cytoplasmic-male sterility (CMS) is a pollen abor-tion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus and continues to be male sterile in the next genera-tion. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmi-cally inherited trait may be a naturally occurring maize trait or a trait introduced through genetic transformation tech-niques.

In another aspect, a tissue culture of regenerable cells of a plant of variety CH010482 is provided. The tissue culture will preferably be capable of regenerating plants capable of expressing all the physiological and morphological charac-teristics of the variety, and of regenerating plants having substantially the same genotype as other plants of the variety. Examples of some of the physiological and mor-phological characteristics of the variety CH010482 include characteristics related to yield, maturity, and kernel quality, each of which is specifically disclosed herein. The regener-able cells in such tissue cultures may, for example, be derived from embryos, meristematic cells, immature tassels, microspores, pollen, leaves, anthers, roots, root tips, silk, flowers, kernels, ears, cobs, husks, or stalks, or from callus or protoplasts derived from those tissues. Still further, the present disclosure provides corn plants regenerated from the tissue cultures, the plants having all the physiological and morphological characteristics of variety CH010482.

In still another aspect, the disclosure provides a method of producing hybrid corn seed comprising crossing a plant of variety CV844363 with a plant of variety CV957256. In a cross, either parent may serve as the male or female. Processes are also provided for producing corn seeds or plants in which the processes generally comprise crossing a first parent corn plant with a second parent corn plant, wherein at least one of the first or second parent corn plants is a plant of the variety designated CH010482. In such crossing, either parent may serve as the male or female parent. These processes may be further exemplified as processes for preparing hybrid corn seed or plants, wherein a first hybrid corn plant is crossed with a second corn plant of a different, distinct variety to provide a hybrid that has, as one of its parents, the hybrid corn plant variety CH010482. In these processes, crossing will result in the production of seed. The seed production occurs regardless of whether the seed is collected or not.

In one embodiment, the first step in "crossing" comprises planting, often in pollinating proximity, seeds of a first and second parent corn plant, and in many cases, seeds of a first corn plant and a second, distinct corn plant. When the plants are not in pollinating proximity, pollination can nevertheless be accomplished by transferring a pollen or tassel bag from one plant to the other as described below.

A second step comprises cultivating or growing the seeds of said first and second parent corn plants into plants that bear flowers (corn bears both male flowers (tassels) and female flowers (silks) in separate anatomical structures on the same plant). A third step comprises preventing self-pollination of the plants, i.e., preventing the silks of a plant from being fertilized by any plant of the same variety, including the same plant. This can be done, for example, by emasculating the male flowers of the first or second parent corn plant, (i.e., treating or manipulating the flowers to prevent pollen production, to produce an emasculated parent corn plant). Self-incompatibility systems may also be used in some hybrid crops for the same purpose. Self-incompat-ible plants still shed viable pollen and can pollinate plants of other varieties but are incapable of pollinating themselves or other plants of the same variety.

A fourth step may comprise allowing cross-pollination to occur between the first and second parent corn plants. When the plants are not in pollinating proximity, this is done by placing a bag, usually paper or glassine, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is no longer viable, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place. Yet another step comprises harvesting the seeds from at least one of the parent corn plants. The harvested seed can be grown to produce a corn plant or hybrid corn plant.

The present disclosure also provides corn seed and plants produced by a process that comprises crossing a first parent corn plant with a second parent corn plant, wherein at least one of the first or second parent corn plants is a plant of the variety designated CH010482. In one embodiment, corn seed and plants produced by the process are first generation hybrid corn seed and plants produced by crossing an inbred with another, distinct inbred. The present disclosure further contemplates seed of an $F_1$ hybrid corn plant. Therefore, certain exemplary embodiments provide an $F_1$ hybrid corn plant and seed thereof, specifically the hybrid variety des-ignated CH010482.

Such a plant can be analyzed by its "genetic comple-ment". This term is used to refer to the aggregate of nucleotide sequences, the expression of which defines the phenotype of, for example, a corn plant, or a cell or tissue of that plant. A genetic complement thus represents the genetic makeup of a cell, tissue, or plant. The disclosure thus provides corn plant cells that have a genetic complement in accordance with the corn plant cells disclosed herein, and plants, seeds and diploid plants containing such cells.

Plant genetic complements may be assessed by genetic marker profiles, and by the expression of phenotypic traits that are characteristic of the expression of the genetic complement, e.g., marker typing profiles. It is known in the art that such complements may also be identified by marker types including, but not limited to, Simple Sequence Repeats (SSRs), Simple Sequence Length Polymorphisms (SSLPs), Randomly Amplified Polymorphic DNAs (RAPDs), DNA Amplification Fingerprinting (DAF), Sequence Character-ized Amplified Regions (SCARs), Arbitrary Primed Poly-

5

6 merase Chain Reaction (AP-PCR), Amplified Fragment Length Polymorphisms (AFLPs), and Single Nucleotide Polymorphisms (SNPs).

In still yet another aspect, the present disclosure provides hybrid genetic complements, as represented by corn plant cells, tissues, plants, and seeds, formed by the combination of a haploid genetic complement of a corn plant with a haploid genetic complement of the same or a different variety. In another aspect, the present disclosure provides a corn plant regenerated from a tissue culture that comprises a hybrid genetic complement.

DETAILED DESCRIPTION

Definitions of Plant Characteristics

Barren Plants: Plants that are barren, i.e., lack an ear with grain, or have an ear with only a few scattered kernels.

Cg: *Colletotrichum graminicola* rating. The rating multiplied by 10 is approximately equal to percent total plant infection.

CLN: Corn Lethal Necrosis (combination of Maize Chlorotic Mottle Virus and Maize Dwarf Mosaic virus) rating. A numerical rating that is based on a 1 to 9 scale of severity in which "1" indicates "most resistant" and "9" indicates "most susceptible."

Cn: *Corynebacterium nebraskense* rating. The rating multiplied by 10 is approximately equal to percent total plant infection.

Cz: *Cercospora zeae-maydis* rating. The rating multiplied by 10 is approximately equal to percent total plant infection.

Dgg: *Diatraea grandiosella* girdling rating. A rating in which the value equals percent plants girdled, and stalk lodged.

Dropped Ears: Ears that have fallen from the plant to the ground.

Dsp: *Diabrotica* species root rating. A rating that is based on a 1 to 9 scale in which "1" indicates "least affected" and "9" indicates "severe pruning."

Ear-Attitude: The attitude or position of the ear at harvest, which is scored as upright, horizontal, or pendant.

Ear-Cob Color: The color of the cob, which is scored as white, pink, red, or brown.

Ear-Cob Diameter: The average diameter of the cob when measured at the midpoint.

Ear-Cob Strength: A measure of mechanical strength of the cobs to breakage, which is scored as strong or weak.

Ear-Diameter: The average diameter of the ear when measured at the midpoint.

Ear-Dry Husk Color: The color of the husks at harvest, which is scored as buff, red, or purple.

Ear-Fresh Husk Color: The color of the husks 1 to 2 weeks after pollination, which is scored as green, red, or purple.

Ear-Husk Bract: The length of an average husk leaf, which is scored as short, medium, or long.

Ear-Husk Cover: The average distance from the tip of the ear to the tip of the husks in which the minimum value is no less than zero.

Ear-Husk Opening: An evaluation of husk tightness at harvest, which is scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence, which is scored as green-yellow, yellow, pink, red, or purple.

Ear-Taper (Shape): The taper or shape of the ear, which is scored as conical, semi-conical, or cylindrical.

Ear-Weight: The average weight of an ear.

Early Stand: The percent of plants that emerge from the ground as determined in the early spring.

ER: Ear rot rating. A rating in which the value approximates percent ear rotted.

Final Stand Count: The number of plants just prior to harvest.

GDUs: Growing degree units. GDUs are calculated by the Barger Method in which the heat units for a 24 h period are calculated as follows: [(Maximum daily temperature+Minimum daily temperature)/2]−50. The highest maximum daily temperature used is 86° F. and the lowest minimum temperature used is 50° F.

GDUs to Shed: The number of growing degree units (GDUs) or heat units required for a variety to have approximately 50% of the plants shedding pollen as measured from time of planting. GDUs to shed is determined by summing the individual GDU daily values from the planting date to the date of 50% pollen shed.

GDUs to Silk: The number of growing degree units (GDUs) for a variety to have approximately 50% of the plants with silk emergence as measured from the time of planting. GDUs to silk is determined by summing the individual GDU daily values from the planting date to the date of 50% silking.

Hc2: *Helminthosporium carbonum* race 2 rating. The rating multiplied by 10 is approximately equal to percent total plant infection.

Hc3: *Helminthosporium carbonum* race 3 rating. The rating multiplied by 10 is approximately equal to percent total plant infection.

Hm: *Helminthosporium maydis* race 0 rating. The rating multiplied by 10 is approximately equal to percent total plant infection.

Ht1: *Helminthosporium turcicum* race 1 rating. The rating multiplied by 10 is approximately equal to percent total plant infection.

Ht2: *Helminthosporium turcicum* race 2 rating. The rating multiplied by 10 is approximately equal to percent total plant infection.

HtG: Chlorotic-lesion type resistance. "+" indicates the presence of Ht chlorotic-lesion type resistance; "−" indicates absence of Ht chlorotic-lesion type resistance; and "+/−" indicates segregation of Ht chlorotic-lesion type resistance. The rating multiplied by 10 is approximately equal to percent total plant infection.

Kernel-Aleurone Color: The color of the aleurone, which is scored as white, pink, tan, brown, bronze, red, purple, pale purple, colorless, or variegated.

Kernel-Cap Color: The color of the kernel cap observed at dry stage, which is scored as white, lemon-yellow, yellow, or orange.

Kernel-Endosperm Color: The color of the endosperm, which is scored as white, pale yellow, or yellow.

Kernel-Endosperm Type: The type of endosperm, which is scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp, which is scored as colorless, red-white crown, tan, bronze, brown, light red, cherry red, or variegated.

Kernel-Row Direction: The direction of the kernel rows on the ear, which is scored as straight, slightly curved, spiral, or indistinct (scattered).

Kernel-Row Number: The average number of rows of kernels on a single ear.

Kernel-Side Color: The color of the kernel side observed at the dry stage, which is scored as white, pale yellow, yellow, orange, red, or brown.

Kernel-Thickness: The distance across the narrow side of the kernel.

Kernel-Type: The type of kernel, which is scored as dent, flint, or intermediate.

Kernel-Weight: The average weight of a predetermined number of kernels.

Kernel-Width: The distance across the flat side of the kernel.

Kz: *Kabatiella zeae* rating. The rating multiplied by 10 is approximately equal to percent total plant infection.

Leaf-Angle: Angle of the upper leaves to the stalk, which is scored as upright (0 to 30 degrees), intermediate (30 to 60 degrees), or lax (60 to 90 degrees).

Leaf-Color: The color of the leaves 1 to 2 weeks after pollination, which is scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination, which is rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, which is scored as absent, basal-weak, basal-strong, weak, or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf when measured at its widest point.

LSS: Late season standability. The value multiplied by 10 is approximately equal to percent plants lodged in disease evaluation plots.

Moisture: The moisture of the grain at harvest.

On1: *Ostrinia nubilalis* 1st brood rating. The rating is based on a 1 to 9 scale in which "1" indicates "resistant" and "9" indicates "susceptible."

On2: *Ostrinia nubilalis* 2nd brood rating. The rating is based on a 1 to 9 scale in which "1" indicates "resistant" and "9" indicates "susceptible."

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale in which the best and worst ratings are "1" and "9", respectively. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating. The rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear when measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes with Brace Roots: The average number of nodes having brace roots per plant.

Stalk-Plant Height: The average height of the plant when measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity) and is usually recorded at the time the ear husks of most entries within a trial have turned a mature color. Scoring is on a 1 to 9 basis in which "1" and "9" are the best and worst score, respectively.

STR: Stalk rot rating. The rating is based on a 1 to 9 scale of severity in which "1" indicates "25% of inoculated internode rotted" and "9" indicates "entire stalk rotted and collapsed."

SVC: Southeastern Virus Complex (combination of Maize Chlorotic Dwarf Virus and Maize Dwarf Mosaic Virus) rating. The numerical rating is based on a 1 to 9 scale of severity in which "1" indicates "most resistant" and "9" indicates "most susceptible."

Tassel-Anther Color: The color of the anthers at 50% pollen shed, which is scored as green-yellow, yellow, pink, red, or purple.

Tassel-Attitude: The attitude of the tassel after pollination, which is scored as open or compact.

Tassel-Branch Angle: The angle of an average tassel branch to the main stem of the tassel, which is scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume, which is scored as present or absent.

Tassel-Glume Color: The color of the glumes at 50% shed, which is scored as green, red, or purple.

Tassel-Length: The length of the tassel, which is measured from the base of the bottom tassel branch to the tassel tip.

Tassel-Peduncle Length: The average length of the tassel peduncle, which is measured from the base of the flag leaf to the base of the bottom tassel branch.

Tassel-Pollen Shed: A visual rating of pollen shed that is determined by tapping the tassel and observing the pollen flow of approximately five plants per entry. The rating is based on a 1 to 9 scale in which "9" indicates "sterile" and "1" indicates "most pollen."

Tassel-Spike Length: The length of the spike, which is measured from the base of the top tassel branch to the tassel tip.

Test Weight: Weight of the grain in pounds for a given volume (bushel) adjusted to 15.5% moisture.

Yield: Yield of grain at harvest adjusted to 15.5% moisture.

Other Definitions

Allele: Any of one or more alternative forms of a gene locus, all of which relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first-generation hybrid ($F_1$) with one of the parental genotypes of the $F_1$ hybrid.

Crossing: The pollination of a female flower of a corn plant, thereby resulting in the production of seed from the flower.

Cross-pollination: Fertilization by the union of two gametes from different plants.

Diploid: A cell or organism having two sets of chromosomes.

Emasculate: The removal of plant male sex organs or the inactivation of the organs with a chemical agent or a cytoplasmic or nuclear genetic factor conferring male sterility.

$F_1$ Hybrid: The first-generation progeny of the cross of two plants.

Genetic Complement: An aggregate of nucleotide sequences, the expression of which sequences defines the phenotype in corn plants, or components of plants including cells or tissue.

Genotype: The genetic constitution of a cell or organism.

Haploid: A cell or organism having one set of the two sets of chromosomes in a diploid.

Marker: A readily detectable phenotype or genotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Genetic loci that contribute, at least in part, to certain numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing or by genome editing of a locus, wherein essentially all the morphological and physiological characteristics of an inbred are recovered in addition to the characteristics conferred by the single locus transferred into the inbred via the backcrossing or genome editing technique. A single locus may comprise one gene, or in the case of transgenic plants, one or more transgenes integrated into the host genome at a single site (locus).

Tissue Culture: A composition comprising isolated cells of the same or a different type or a collection of such cells organized into parts of a plant.

Three-way cross hybrid: A hybrid plant produced by crossing a first inbred plant with the $F_1$ hybrid progeny derived from crossing a second inbred plant with a third inbred plant.

Transgene: A genetic sequence which has been introduced into the nuclear or cytoplasmic components of the genome of a corn plant by a genetic transformation technique.

Variety Descriptions

In accordance with one aspect of the present disclosure, there is provided a novel hybrid corn plant variety designated CH010482. Hybrid variety CH010482 was produced from a cross of the inbred varieties designated CV844363 and CV957256. The inbred parents have been self-pollinated and ear-rowed enough generations with careful attention paid to uniformity of plant type to show uniformity and stability within the limits of environmental influence.

In accordance with one aspect, there is provided a corn plant having the physiological and morphological characteristics of corn plant CH010482. An analysis of such morphological traits was carried out, the results of which are presented in Table 1.

TABLE 1

| Morphological Traits for Hybrid Variety CH010482 | | |
|---|---|---|
| | CHARACTERISTIC | VALUE |
| 1 | STALK | |
| | Plant Height (cm) | 283.5 |
| | Ear Height (cm) | 118.9 |
| | Anthocyanin | ABSENT |
| | Brace Root Color | ABSENT |
| | Internode Direction | STRAIGHT |
| | Internode Length (cm) | 19.3 |
| 2 | LEAF | |
| | Color | DARK GREEN |
| | Length (cm) | 98.7 |
| | Width (cm) | 10.3 |
| | Sheath Anthocyanin | ABSENT |
| | Sheath Pubescence | HEAVY |
| | Marginal Waves | FEW |
| | Longitudinal Creases | FEW |
| 3 | TASSEL | |
| | Length (cm) | 48 |
| | Peduncle Length (cm) | 8.2 |
| | Branch Number | 9 |
| | Anther Color | YELLOW |
| | Glume Color | GREEN & MEDIUM GREEN |
| | Glume Band | ABSENT |
| 4 | EAR | |
| | Silk Color | YELLOW |
| | Number Per Stalk | 1 |
| | Position | UPRIGHT |
| | Length (cm) | 18.7 |

TABLE 1-continued

| Morphological Traits for Hybrid Variety CH010482 | |
| --- | --- |
| CHARACTERISTIC | VALUE |
| Shape | CYLINDRICAL |
| Diameter (mm) | 48.2 |
| Shank Length (cm) | 9.3 |
| Husk Bract | SHORT |
| Husk Cover (cm) | 3.5 |
| Husk Opening | MODERATE |
| Husk Color Fresh | GREEN & MEDIUM GREEN |
| Husk Color Dry | BUFF |
| Cob Diameter (mm) | 24.3 |
| Cob Color | RED |
| Shelling Percent | 90.5 |
| 5 KERNEL | |
| Row Number | 15.6 |
| Number Per Row | 37.6 |
| Row Direction | STRAIGHT |
| Type | DENT |
| Cap Color | DEEP YELLOW |
| Side Color | YELLOW - ORANGE |
| Length (depth) (mm) | 13.9 |
| Width (mm) | 8.3 |
| Thickness (mm) | 4.8 |
| Endosperm Type | NORMAL |
| Endosperm Color | YELLOW |

*These are typical values. Values may vary due to environment. Other values that are substantially equivalent are within the scope of the disclosure. Substantially equivalent refers to quantitative traits that when compared do not show statistical differences of their means In accordance with another aspect of the present disclosure, there is provided a corn plant having the morphological characteristics of corn plant CV844363. A description of the morphological and physiological characteristics of corn plant CV844363 is presented in Table 2.

TABLE 2

| Morphological and Physiological Traits for Corn Variety CV844363 | | |
| --- | --- | --- |
| CHARACTERISTIC | | VALUE |
| 1 | STALK | |
| | Plant Height (cm) | 214.9 |
| | Ear Height (cm) | 73.8 |
| | Anthocyanin | ABSENT |
| | Brace Root Color | FAINT |
| | Internode Direction | STRAIGHT |
| | Internode Length (cm) | 16.3 |
| 2 | LEAF | |
| | Color | DARK GREEN |
| | Length (cm) | 77.4 |
| | Width (cm) | 8.6 |
| | Sheath Anthocyanin | ABSENT |
| | Sheath Pubescence | HEAVY |
| | Marginal Waves | FEW |
| | Longitudinal Creases | FEW |
| 3 | TASSEL | |
| | Length (cm) | 38.7 |
| | Peduncle Length (cm) | 7.4 |
| | Branch Number | 5.3 |
| | Anther Color | YELLOW |
| | Glume Color | GREEN |
| | Glume Band | ABSENT |
| 4 | EAR | |
| | Silk Color | YELLOW |
| | Number Per Stalk | 1 |
| | Position | UPRIGHT |
| | Length (cm) | 17 |
| | Shape | SEMI CONICAL |
| | Diameter (mm) | 41.7 |
| | Shank Length (cm) | 6.3 |
| | Husk Bract | SHORT |
| | Husk Cover (cm) | 5 |
| | Husk Opening | TIGHT |

TABLE 2-continued

| Morphological and Physiological Traits for Corn Variety CV844363 | | |
| --- | --- | --- |
| CHARACTERISTIC | | VALUE |
| | Husk Color Fresh | GREEN |
| | Husk Color Dry | BUFF |
| | Cob Diameter (mm) | 24.3 |
| | Cob Color | RED |
| | Shelling Percent | 86 |
| 5 | KERNEL | |
| | Row Number | 15.9 |
| | Number Per Row | 30.4 |
| | Row Direction | STRAIGHT |
| | Type | DENT |
| | Cap Color | DEEP YELLOW |
| | Side Color | DEEP YELLOW |
| | Length (depth) (mm) | 11.1 |
| | Width (mm) | 8.1 |
| | Thickness (mm) | 4.8 |
| | Endosperm Type | NORMAL |
| | Endosperm Color | YELLOW |

*These are typical values. Values may vary due to environment. Other values that are substantially equivalent are within the scope of the disclosure. Substantially equivalent refers to quantitative traits that when compared do not show statistical differences of their means In accordance with another aspect of the present disclosure, there is provided a corn plant having the morphological characteristics of corn plant CV957256. A description of the morphological and physiological characteristics of corn plant CV957256 is presented in Table 3.

TABLE 3

| Morphological and Physiological Traits for Corn Variety CV957256 | | |
| --- | --- | --- |
| CHARACTERISTIC | | VALUE |
| 1 | STALK | |
| | Plant Height (cm) | 224.5 |
| | Ear Height (cm) | 83.5 |
| | Anthocyanin | BASAL WEAK |
| | Brace Root Color | FAINT |
| | Internode Direction | STRAIGHT |
| | Internode Length (cm) | 16.9 |
| 2 | LEAF | |
| | Color | GREEN |
| | Length (cm) | 82.5 |
| | Width (cm) | 9.5 |
| | Sheath Anthocyanin | BASAL WEAK |
| | Sheath Pubescence | MEDIUM |
| | Marginal Waves | FEW |
| | Longitudinal Creases | FEW |
| 3 | TASSEL | |
| | Length (cm) | 41.3 |
| | Peduncle Length (cm) | 5.4 |
| | Branch Number | 8.1 |
| | Anther Color | YELLOW |
| | Glume Color | GREEN |
| | Glume Band | ABSENT |
| 4 | EAR | |
| | Silk Color | YELLOW |
| | Number Per Stalk | 1 |
| | Position | UPRIGHT |
| | Length (cm) | 15.9 |
| | Shape | SEMI CONICAL |
| | Diameter (mm) | 41.9 |
| | Shank Length (cm) | 7.3 |
| | Husk Bract | SHORT |
| | Husk Cover (cm) | 4.7 |
| | Husk Opening | TIGHT |
| | Husk Color Fresh | GREEN |
| | Husk Color Dry | BUFF |
| | Cob Diameter (mm) | 25.2 |
| | Cob Color | PINK |
| | Shelling Percent | 87.2 |

13

TABLE 3-continued

Morphological and Physiological
Traits for Corn Variety CV957256

| | CHARACTERISTIC | VALUE |
|---|---|---|
| 5 | KERNEL | |
| | Row Number | 15.1 |
| | Number Per Row | 28.1 |
| | Row Direction | SLIGHTLY CURVED |
| | Type | INTERMEDIATE |
| | Cap Color | YELLOW ORANGE |
| | Side Color | ORANGE |
| | Length (depth) (mm) | 10.5 |
| | Width (mm) | 8.7 |
| | Thickness (mm) | 5 |
| | Endosperm Type | NORMAL |
| | Endosperm Color | ORANGE |

*These are typical values. Values may vary due to environment. Other values that are substantially equivalent are within the scope of the disclosure. Substantially equivalent refers to quantitative traits that when compared do not show statistical differences of their means.

Deposit Information

A deposit of at least 625 seeds of inbred parent plant varieties CV844363 (U.S. patent application Ser. No. 18/391,793, published as U.S. Patent Application Publication No. 2025/0204393) and CV957256 (U.S. patent application Ser. No. 18/391,774, published as U.S. Patent Application Publication No. 2025/0204392) has been made with the Provasoli-Guillard National Center for Marine Algae and Microbiota (NCMA) at Bigelow Laboratory for Ocean Sciences, 60 Bigelow Drive, East Boothbay, ME 04544 USA, and assigned NCMA Accession No. 202306063 and NCMA Accession No. 202306065, respectively. The dates of deposit with the NCMA are Jun. 15, 2023 and Jun. 15, 2023, respectively. All restrictions upon availability of the deposits to the public will be irrevocably removed upon granting of the patent, and the deposits are intended to meet all the requirements of the Budapest Treaty and 37 C.F.R. § 1.801-1.809. Access to the deposits will be available during the pendency of the application to the Commissioner of Patents and Trademarks and persons determined by the Commissioner to be entitled thereto upon request. The deposits have been accepted under the Budapest Treaty and will be maintained in the NCMA Depositary, which is a public depositary, for a period of 30 years, or 5 years after the most recent request, or for the enforceable life of the patent, whichever is longer, and will be replaced if it becomes nonviable during that period. Applicant does not waive any infringement of their rights granted under this patent or under the Plant Variety Protection Act (7 U.S.C. 2321 et seq.).

Further Embodiments

In one embodiment, compositions are provided comprising a seed of corn variety CH010482 comprised in plant seed cultivation media. Plant seed cultivation media are well known to those of skill in the art and include, but are in no way limited to, soil or synthetic cultivation medium. Plant seed cultivation media can provide adequate physical support for seeds and can retain moisture and/or nutritional components. Synthetic plant cultivation media are also well known in the art and may, in certain embodiments, comprise polymers or hydrogels.

In certain further aspects, the disclosure provides plants modified to include at least a first trait. Such plants may, in one embodiment, be developed by a plant breeding technique called backcrossing, wherein essentially all the morphological and physiological characteristics of a variety are recovered in addition to a genetic locus transferred into the hybrid via the backcrossing technique. By essentially all the morphological and physiological characteristics, it is meant that all the characteristics of a plant are recovered that are otherwise present when compared in the same environment, other than an occasional variant trait that might arise during backcrossing or direct introduction of a transgene. In one embodiment, such traits may be determined, for example, relative to the traits listed in Table 1 as determined at the 5% significance level when grown under the same environmental conditions.

Backcrossing methods can be used to improve or introduce a trait in a hybrid via modification of its inbred parent(s). The term backcrossing as used herein refers to the repeated crossing of a hybrid progeny back to one of the parental corn plants for that hybrid. The parental corn plant which contributes the locus or loci for the trait is termed the nonrecurrent or donor parent. This terminology refers to the fact that the nonrecurrent parent is used one time in the backcross protocol and therefore does not recur.

The parental corn plant to which the locus or loci from the nonrecurrent parent are transferred is known as the recurrent parent as it is used for several rounds in the backcrossing protocol. In a typical backcross protocol, the original parent hybrid of interest (recurrent parent) is crossed to a second variety (nonrecurrent parent) that carries the genetic locus of interest to be transferred. The resulting progeny from this cross are then crossed again to the recurrent parent and the process is repeated until a corn plant is obtained wherein essentially all the morphological and physiological characteristics of the recurrent parent are recovered in the converted plant, in addition to the transferred locus from the nonrecurrent parent. The backcross process may be accelerated using genetic markers, such as SSR, RFLP, SNP or AFLP markers to identify plants with the greatest genetic complement from the recurrent parent.

The selection of a suitable recurrent parent is an important step for a successful backcrossing procedure. The goal of a backcross protocol is to add or substitute one or more new traits in the original inbred and hybrid progeny therefrom. To accomplish this, a genetic locus of the recurrent parent is modified or substituted with the locus from the nonrecurrent parent, while retaining essentially all the rest of the genetic complement, and therefore the morphological and physiological constitution of the original plant. The choice of the nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, waxy starch, herbicide resistance, resistance to bacterial, fungal, or viral disease, insect resistance, male fertility and enhanced nutritional quality. These genes are generally inherited through the nucleus but may be inherited through the cytoplasm. Some known exceptions to this are genes for male sterility, some of which are inherited cytoplasmically, but still act as a single locus trait.

Direct selection may be applied when a genetic locus acts as a dominant trait. An example of a dominant trait is the herbicide resistance trait. For this selection process, the progeny of the initial cross are sprayed with the herbicide prior to the backcrossing. The spraying eliminates any plants which do not have the herbicide resistance characteristic, and only those plants which have the herbicide resistance gene are used in the subsequent backcross. This process is then repeated for all additional backcross generations.

Many useful traits are those which are introduced by genetic transformation techniques. Methods for the genetic transformation of corn are known to those of skill in the art.

Included among various plant transformation techniques are methods permitting the site-specific modification of a plant genome. These modifications can include, but are not limited to, site-specific mutations, deletions, insertions, and replacements of nucleotides. These modifications can be made anywhere within the genome of a plant, for example, in genomic elements, including, among others, coding sequences, regulatory elements, and non-coding DNA sequences. Any number of such modifications can be made, and that number of modifications may be made in any order or combination, for example, simultaneously all together or one after another. Such methods may be used to modify a particular trait conferred by a locus. The techniques for making such modifications by genome editing are well known in the art and include, for example, use of CRISPR-Cas systems, zinc-finger nucleases (ZFNs), and transcription activator-like effector nucleases (TALENs), among others.

It is understood to those of skill in the art that a transgene need not be directly transformed into a plant, as techniques to produce stably transformed corn plants that pass single loci to progeny by Mendelian inheritance is well known in the art. Such loci may therefore be passed from parent plant to progeny plants by standard plant breeding techniques that are well known in the art.

A. Male Sterility

Examples of genes conferring male sterility are well known in the art. Male sterility genes can increase the efficiency with which hybrids are made, in that they eliminate the need to physically emasculate the corn plant used as a female in each cross.

When one desires to employ male-sterility systems with a corn plant in accordance with the disclosure, it may be beneficial to also utilize one or more male-fertility restorer genes. For example, when cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful when the vegetative tissue of the corn plant is utilized, e.g., for silage, but in most cases, the seeds will be deemed the most valuable portion of the crop, so fertility of the hybrids in these crops must be restored. Therefore, one aspect of the current disclosure concerns the hybrid corn plant CH010482 comprising a genetic locus capable of restoring male fertility in an otherwise male-sterile plant. Examples of male-sterility genes and corresponding restorers which could be employed with the plants of the disclosure are well known to those of skill in the art of plant breeding.

B. Herbicide Resistance

Numerous herbicide resistance genes are known and may be employed with the disclosure. A non-limiting example is a gene conferring resistance to an herbicide that inhibits the growing point or meristem such as imidazolinone or sulfonylurea herbicides. As imidazolinone and sulfonylurea herbicides are acetolactate synthase (ALS)-inhibiting herbicides that prevent the formation of branched chain amino acids, exemplary genes in this category code for ALS and AHAS enzymes are well known in the art. As a non-limiting example, a gene may be employed to confer resistance to the exemplary sulfonylurea herbicide nicosulfuron.

Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. Non-limiting examples of EPSPS transformation events conferring glyphosate resistance are well known in the art.

Genes are also known that confer resistance to herbicides that inhibit photosynthesis such as, for example, triazine herbicides (psbA and gs+ genes) and benzonitrile herbicides (nitrilase gene). As a non-limiting example, a gene may confer resistance to the exemplary benzonitrile herbicide bromoxynil.

Plant cytochrome P450-mediated detoxification of multiple, chemically unrelated classes of herbicides are well known in the art. Modified bacterial genes have been successfully demonstrated to confer resistance to atrazine, an herbicide that binds to the plastoquinone-binding membrane protein $Q_B$ in photosystem II to inhibit electron transport.

C. Waxy Starch

The waxy characteristic is an example of a recessive trait. In this example, the progeny resulting from the first backcross generation ($BC_1$) must be grown and selfed. A test is then run on the selfed seed from the $BC_1$ plant to determine which $BC_1$ plants carried the recessive gene for the waxy trait. In other recessive traits additional progeny testing, for example growing additional generations such as the $BC_1F_1$, may be required to determine which plants carry the recessive gene.

D. Disease Resistance

Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains.

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

A virus-specific antibody may also be used. Transgenic plants expressing recombinant antibody genes may be protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production.

Transgenic plants expressing a barley ribosome-inactivating gene have an increased resistance to fungal disease. Plant defensins may be used to provide resistance to fungal pathogens.

E. Insect Resistance

One example of an insect resistance gene includes a *Bacillus thuringiensis* (Bt) protein, a derivative thereof or a synthetic polypeptide modeled thereon. A vitamin-binding protein may also be used, such as avidin. This application teaches the use of avidin and avidin homologues as larvicides against insect pests. Yet another insect resistance gene is an enzyme inhibitor, for example, a protease or proteinase inhibitor or an amylase inhibitor. An insect-specific hormone or pheromone may also be used. Still other examples include an insect-specific antibody, or an immunotoxin derived therefrom and a developmental-arrestive protein.

F. Modified Fatty Acid, Phytate, and Carbohydrate Metabolism

Genes may be used conferring modified fatty acid metabolism, in terms of content and quality.

Phytate metabolism may also be modified by introduction of a phytase-encoding gene to enhance breakdown of phytate, adding more free phosphate to the transformed plant. In corn, this, for example, could be accomplished by cloning and then reintroducing DNA associated with the single allele which is responsible for corn mutants characterized by low levels of phytic acid.

A number of genes are known that may be used to alter carbohydrate metabolism. For example, plants may be transformed with a gene coding for an enzyme that alters the branching pattern of starch.

G. Resistance to Abiotic Stress

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought. Overexpression of superoxide dismutase can be used to protect against superoxides.

H. Additional Traits

Additional traits can be introduced into the corn variety of the present disclosure. A non-limiting example of such a trait is a coding sequence which decreases RNA and/or protein levels. The decreased RNA and/or protein levels may be achieved through RNAi methods.

Another trait that may find use with the corn varieties a sequence which allows for site-specific recombination. Examples of such sequences include the FRT sequence used with the FLP recombinase; and the LOX sequence used with CRE recombinase. The recombinase genes can be encoded at any location within the genome of the corn plant and are active in the hemizygous state.

It may also be desirable to make corn plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases.

In addition to the modification of oil, fatty acid or phytate content described above, it may additionally be beneficial to modify the amounts or levels of other compounds. For example, the amount or composition of antioxidants can be altered directly or via manipulation of an antioxidant biosynthetic pathway.

Additionally, seed amino acid content may be manipulated.

It may be beneficial to modify the corn plant height. Short stature corn has stronger stalks due to the reduced height, which are less likely to break or fall over in high winds. Shorter plants also make the corn fields more accessible to standard ground equipment longer into the growing season, creating the opportunity for more timely, precise applications of crop protection products and other inputs. Short stature corn may be produced via techniques including but not limited to conventional breeding, biotechnology, and gene editing techniques. Corn plants comprising non-natural brachytic mutations results in plants with reduced height. Additionally, short stature corn may be produced by altering the plant's gibberellin metabolism via suppression, mutagenesis and/or editing of specific gibberellin oxidase genes. Techniques for manipulating corn height are well known in the art.

I. Origin and Breeding History of an Exemplary Introduced Trait

Provided by the disclosure is a hybrid plant in which one or more of the parents comprise an introduced trait. Such a plant may be defined as comprising a single locus conversion. Exemplary procedures for the preparation of such single locus conversions are well known in the art.

An example of a single locus conversion is 85DGD1. 85DGD1 MLms is a conversion of 85DGD1 to cytoplasmic male sterility. 85DGD1 MLms was derived using backcross methods. 85DGD1 (a proprietary inbred of Monsanto Company) was used as the recurrent parent and MLms, a germplasm source carrying ML cytoplasmic sterility, was used as the nonrecurrent parent. The breeding history of the converted inbred 85DGD1 MLms can be summarized as follows:

| | |
|---|---|
| Hawaii Nurseries Planting Date Apr. 2, 1992 | Made up S-O: Female row 585 male row 500 |
| Hawaii Nurseries Planting Date Jul. 15, 1992 | S-O was grown, and plants were backcrossed times 85DGD1 (rows 444 ′ 443) |
| Hawaii Nurseries Planting Date Nov. 18, 1992 | Bulked seed of the BC₁ was grown and backcrossed times 85DGD1 (rows V3-27 ′ V3-26) |
| Hawaii Nurseries Planting Date Apr. 2, 1993 | Bulked seed of the BC₂ was grown and backcrossed times 85DGD1 (rows 37 ′ 36) |
| Hawaii Nurseries Planting Date Jul. 14, 1993 | Bulked seed of the BC₃ was grown and backcrossed times 85DGD1 (rows 99 ′ 98) |

-continued

| Hawaii Nurseries Planting Date Oct. 28, 1993 | Bulked seed of BC$_4$ was grown and backcrossed times 85DGD1 (rows KS-63 ' KS-62) |
|---|---|
| Summer 1994 | A single ear of the BC$_5$ was grown and backcrossed times 85DGD1 (MC94-822 ' MC94-822-7) |
| Winter 1994 | Bulked seed of the BC$_6$ was grown and backcrossed times 85DGD1 (3Q-1 ' 3Q-2) |
| Summer 1995 | Seed of the BC$_7$ was bulked and named 85DGD1 MLms. |

As described, techniques to produce corn plants with added traits are well known in the art. A non-limiting example of such a procedure one of skill in the art could use for preparation of a hybrid corn plant CH010482 comprising an added trait is as follows:

(a) crossing a parent of hybrid corn plant CH010482 such as CV844363 and/or CV957256 to a second (nonrecurrent) corn plant comprising a locus to be converted in the parent;

(b) selecting at least a first progeny plant resulting from the crossing and comprising the locus;

(c) crossing the selected progeny to the parent line of corn plant CH010482;

(d) repeating steps (b) and (c) until a parent line of variety CH010482 is obtained comprising the locus; and (e) crossing the converted parent with the second parent to produce hybrid variety CH010482 comprising a trait.

Following these steps, essentially any locus may be introduced into hybrid corn variety CH010482. For example, molecular techniques allow introduction of any given locus, without the need for phenotypic screening of progeny during the backcrossing steps.

PCR and Southern hybridization are two examples of molecular techniques that may be used for confirmation of the presence of a given locus and thus conversion of that locus. The techniques are carried out as follows: Seeds of progeny plants are grown, and DNA isolated from leaf tissue. Approximately one gram of leaf tissue is lyophilized overnight in 15 ml polypropylene tubes. Freeze-dried tissue is ground to a powder in the tube using a glass rod. Powdered tissue is mixed thoroughly with 3 ml extraction buffer (7.0M urea, 0.35M NaCl, 0.05M Tris-HCl PH 8.0, 0.01M EDTA, 1% sarcosine). Tissue/buffer homogenate is extracted with 3 ml phenol/chloroform. The aqueous phase is separated by centrifugation and precipitated twice using $\frac{1}{10}$ volume of 4.4M ammonium acetate pH 5.2, and an equal volume of isopropanol. The precipitate is washed with 75% ethanol and resuspended in 100-500 μl TE (0.01M Tris-HCl, 0.001M EDTA, pH 8.0). The DNA may then be screened as desired for presence of the locus.

For PCR, 200-1000 ng genomic DNA from the progeny plant being screened is added to a reaction mix containing 10 mM Tris-HCl pH 8.3, 1.5 mM MgCl$_2$, 50 mM KCl, 0.1 mg/ml gelatin, 200 μM each dATP, dCTP, dGTP, dTTP, 20% glycerol, 2.5 units Taq DNA polymerase and 0.5 μM each of forward and reverse DNA primers that span a segment of the locus being converted. The reaction is run in a thermal cycling machine 3 minutes at 94 C, 39 repeats of the cycle 1 minute at 94 C, 1 minute at 50 C, 30 seconds at 72 C, followed by 5 minutes at 72 C. Twenty μl of each reaction mix is run on a 3.5% NuSieve gel in TBE buffer (90 mM Tris-borate, 2 mM EDTA) at 50V for two to four hours. The amplified fragment is detected using an agarose gel. Detection of an amplified fragment corresponding to the segment of the locus spanned by the primers indicates the presence of the locus.

For Southern analysis, plant DNA is restricted, separated in an agarose gel, and transferred to a Nylon filter in 10×SCP (20 SCP: 2M NaCl, 0.6M disodium phosphate, 0.02M disodium EDTA) according to standard methods. Locus DNA or RNA sequences are labeled, for example, radioactively with $^{32}$P by random priming. Filters are prehybridized in 6×SCP, 10% dextran sulfate, 2% sarcosine, and 500 μg/ml denatured salmon sperm DNA. The labeled probe is denatured, hybridized to the filter, and washed in 2×SCP, 1% SDS at 65° C. for 30 minutes and visualized by autoradiography using Kodak XAR5 film. Presence of the locus is indicated by detection of restriction fragments of the appropriate size.

Tissue Cultures and In Vitro Regeneration of Corn Plants

A further aspect relates to tissue cultures of the corn plant designated CH010482. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, ears, cobs, leaves, husks, stalks, roots, root tips, anthers, silk, and the like. In one embodiment, the tissue culture comprises embryos, protoplasts, meristematic cells, pollen, leaves, or anthers derived from immature tissues of these plant parts. Means for preparing and maintaining plant tissue cultures are well known in the art. By way of example, a tissue culture comprising organs such as tassels or anthers has been used to produce regenerated plants.

One type of tissue culture is tassel/anther culture. Tassels contain anthers which in turn enclose microspores. Microspores develop into pollen. For anther/microspore culture, if tassels are the plant composition, they can be selected at a stage when the microspores are uninucleate, that is, include only 1, rather than 2 or 3 nuclei. Methods to determine the correct stage are well known to those skilled in the art and include mitramycin fluorescent staining, trypan blue, and acetocarmine squashing. The mid-uninucleate microspore stage has been found to be the developmental stage most responsive to the subsequent methods disclosed to produce plants.

Although microspore-containing plant organs such as tassels can be pretreated at any cold temperature below about 25° C., a range of 4° C. to 25° C. may be preferred, and a range of 8° C. to 14° C. may be particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture. Exemplary methods of microspore culture are well known in the art.

Although not required, when tassels are employed as the plant organ, it is beneficial to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When one elects to employ tassels directly, tassels are generally pretreated at a cold temperature for a predefined time, often at 10° C. for about 4 days. After pretreatment of a whole tassel at a cold temperature, dissected anthers are further pretreated in an environment that diverts microspores from their developmental pathway. The function of the preculture medium is to switch the developmental program from one of pollen development to that of embryoid/callus development. An embodiment of such an environment in the form of a preculture medium includes a sugar alcohol, for example mannitol or sorbitol, inositol, or the like. An exemplary synergistic combination is the use of mannitol at a temperature of about 10° C. for a period ranging from about 10 to 14 days. In one embodiment, 3 ml of 0.3M mannitol combined with 50 mg/l of ascorbic acid, silver nitrate, and colchicine is used for incubation of anthers at 10° C. for between 10 and 14 days. Another embodiment is to substitute sorbitol for mannitol. The colchicine produces chromosome doubling at this early stage. The chromosome doubling agent is generally only present at the preculture stage.

It is believed that the mannitol or other similar carbon structures or environmental stress induce starvation and function to force microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in 104 microspores, have resulted from using these methods.

To isolate microspores, an isolation media is used. An isolation media is used to separate microspores from the anther walls while maintaining their viability and embryogenic potential. An illustrative embodiment of an isolation media includes a 6% sucrose or maltose solution combined with an antioxidant such as 50 mg/l of ascorbic acid, 0.1 mg/l biotin, and 400 mg/l of proline, combined with 10 mg/l of nicotinic acid and 0.5 mg/l AgNO$_3$. In another embodiment, the biotin and proline are omitted.

An isolation media preferably has a higher antioxidant level when it is used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably, from about 50 mg/l to about 100 mg/l.

One can find particular benefit in employing a support for the microspores during culturing and subculturing. Any support that maintains the cells near the surface can be used. An illustrative embodiment of a solid support is a TRANSWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as a circular support material which is capable of floating slightly above the bottom of a tissue culture vessel, for example, a petri dish, of about a 60- or 100-mm size, although any other laboratory tissue culture vessel will suffice. In an illustrative embodiment, a raft is about 55 mm in diameter.

Culturing isolated microspores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids to full strength medium containing activated charcoal and solidified with, for example, GELRITE™ (solidifying agent).

The liquid medium passes through the mesh while the microspores are retained and supported at the medium-air interface. The surface tension of the liquid medium in the petri dish causes the raft to float. The liquid may pass through the mesh; consequently, the microspores stay on top. The mesh remains on top of the total volume of liquid medium.

The culture vessels can be further defined as either (1) a bilayer 60 mm petri plate wherein the bottom 2 ml of medium are solidified with 0.7% agarose overlaid with 1 mm of liquid containing the microspores; (2) a nylon mesh raft wherein a wafer of nylon is floated on 1.2 ml of medium and 1 ml of isolated microspores is pipetted on top; or (3) TRANSWELL® plates wherein isolated microspores are pipetted onto membrane inserts which support the microspores at the surface of 2 ml of medium.

Examples of processes of tissue culturing and regeneration of corn are described in, for example, European Patent Application Publication No. EP0160390, PCT Application WO 95/06128, and U.S. Pat. No. 5,736,369.

Processes of Crossing Corn Plants and the Corn Plants Produced by Such Crosses

The present disclosure provides processes of preparing novel corn plants and corn plants produced by such processes. In accordance with such a process, a first parent corn plant may be crossed with a second parent corn plant wherein the first and second corn plants are the parent lines of hybrid corn plant variety CH010482, or wherein at least one of the plants is of hybrid corn plant variety CH010482.

Corn plants (Zea mays L.) can be crossed by either natural or mechanical techniques. Natural pollination occurs in corn when the wind blows pollen from the tassels to the silks that protrude from the tops of the recipient ears. Mechanical pollination can be affected either by controlling the types of pollen that can blow onto the silks or by pollinating by hand. In one embodiment, crossing comprises the steps of:

(a) planting in pollinating proximity seeds of a first and a second parent corn plant, and preferably, seeds of a first inbred corn plant and a second, distinct inbred corn plant;

(b) cultivating or growing the seeds of the first and second parent corn plants into plants that bear flowers;

(c) emasculating flowers of either the first or second parent corn plant, i.e., treating the flowers to prevent pollen production, or alternatively, using as the female parent a male sterile plant, thereby providing an emasculated parent corn plant;

(d) allowing natural cross-pollination to occur between the first and second parent corn plants;

(e) harvesting seeds produced on the emasculated parent corn plant; and, when desired, (f) growing the harvested seed into a corn plant, preferably, a hybrid corn plant.

Parental plants are typically planted in pollinating proximity to each other by planting the parental plants in alternating rows, in blocks or in any other convenient planting pattern. When the parental plants differ in timing of sexual maturity, it may be desired to plant the slower maturing plant first, thereby ensuring the availability of pollen from the male parent during the time at which silks on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, if plant CH010482 is employed as the male parent, the tassels of the other parental plant are removed from all plants employed as the female parental plant to avoid self-pollination. The detasseling can be achieved manually but also can be done by machine. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor which causes resistance to the emasculating effects of the chemical agent. Gametocides affect processes or cells involved in the development, maturation, or release of pollen. Plants treated with such gametocides are rendered male sterile, but typically remain female fertile. The use of chemical gametocides is described in the art, for example, the use of Roundup herbicide in combination with glyphosate tolerant corn plants to produce male sterile corn plants.

Following emasculation, the plants are then typically allowed to continue to grow, and natural cross-pollination occurs because of the action of wind, which is normal in the pollination of grasses, including corn. As a result of the emasculation of the female parent plant, all the pollen from the male parent plant is available for pollination because tassels, and thereby pollen bearing flowering parts, have been previously removed from all plants of the plant being used as the female in the hybridization. Of course, during this hybridization procedure, the parental varieties are grown such that they are isolated from other corn fields to minimize or prevent any accidental contamination of pollen from foreign sources. These isolation techniques are well within the skill of those skilled in this art.

Both parental plants of corn may be allowed to continue to grow until maturity or the male rows may be destroyed after flowering is complete. Only the ears from the female parental plants are harvested to obtain seeds of a novel $F_1$ hybrid. The novel $F_1$ hybrid seed produced can then be planted in a subsequent growing season in commercial fields or, alternatively, advanced in breeding protocols for purposes of developing novel inbred lines.

Alternatively, in another embodiment, one or both first and second parent corn plants can be from variety CH010482. Thus, any corn plant produced using corn plant CH010482 forms a part of the disclosure. As used herein, crossing can mean selfing, backcrossing, crossing to another or the same variety, crossing to populations, and the like. All corn plants produced using the corn variety CH010482 as a parent are, therefore, within the scope of this disclosure.

One use of the instant corn variety is in the production of hybrid seed. Any time the corn plant CH010482 is crossed with another, different, corn plant, a corn hybrid plant is produced. As such, hybrid corn plant can be produced by crossing CH010482 with any second corn plant. Any other corn plant can be used to produce a corn plant that has corn plant CH010482 as one parent. All that is required is that the second plant be fertile, which corn plants naturally are, and that the plant is not corn variety CH010482.

The goal of the process of producing an $F_1$ hybrid is to manipulate the genetic complement of corn to generate new combinations of genes which interact to yield new or improved traits (phenotypic characteristics). A process of producing an $F_1$ hybrid typically begins with the production of one or more inbred plants. Those plants are produced by repeated crossing of ancestrally related corn plants to try to combine certain genes within the inbred plants.

The development of new inbred varieties using one or more starting varieties is well known in the art. In accordance with the invention, novel varieties may be created by crossing a corn variety, followed by multiple generations of breeding according to such well known methods. New varieties may be created by crossing a corn variety with any second plant. In selecting such a second plant to cross for the purpose of developing novel inbred lines, it may be desired to choose those plants which either themselves exhibit one or more desirable characteristics or which exhibit the desirable characteristic(s) when in hybrid combination. Examples of potentially desirable characteristics include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Once initial crosses have been made with a corn variety, inbreeding takes place to produce new inbred varieties. Inbreeding requires manipulation by human breeders. Even in the extremely unlikely event inbreeding rather than cross-breeding occurred in natural corn, achievement of complete inbreeding cannot be expected in nature due to well-known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or each genotype can complement the other. If the two original parental genotypes do not provide all the desirable characteristics, other genotypes can be included in the breeding population. Superior plants that are the products of these crosses are selfed and selected in successive generations. Each succeeding generation becomes more homogeneous because of self-pollination and selection. Typically, this method of breeding involves five or more generations of selfing and selection. After at least five generations, the inbred plant is considered genetically pure.

Uniform lines of new varieties may also be developed by way of doubled haploids. This technique allows the creation of true breeding lines without the need for multiple generations of selfing and selection. In this manner true breeding lines can be produced in as little as one generation. Haploid induction systems have been developed for various plants to produce haploid tissues, plants, and seeds. The haploid induction system can produce haploid plants from any genotype by crossing with an inducer line. Inducer lines and methods for obtaining haploid plants are known in the art.

Haploid embryos may be produced, for example, from microspores, pollen, anther cultures, or ovary cultures. The haploid embryos may then be doubled autonomously, or by chemical treatments (e.g., colchicine treatment). Alternatively, haploid embryos may be grown into haploid plants and treated to induce chromosome doubling. In either case, fertile homozygous plants are obtained. In accordance with the disclosure, any of such techniques may be used in connection with a plant of the disclosure and progeny thereof to achieve a homozygous line.

Corn has a diploid phase which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, leading to reduced vigor, less kernels, weak and/or poor growth, production of inbred plants is an unpredictable and arduous process. Under some conditions, heterozygous advantage at some loci effectively bars perpetuation of homozygosity.

A single cross hybrid corn variety is the cross of two inbred plants, each of which has a genotype which complements the genotype of the other. Typically, $F_1$ hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)× (C×D).

Thousands of corn varieties are known to those of skill in the art, any one of which could be crossed with corn plant CH010482 to produce a hybrid plant. Estimates place the number of different corn accessions in gene banks around the world at around 50,000. The Maize Genetics Cooperation Stock Center, which is supported by the U.S. Department of Agriculture, has a total collection of over 80,000 individually pedigreed samples (available on the World Wide Web at maizecoop.cropsci.uiuc.edu/).

When the corn plant CH010482 is crossed with another plant to yield progeny, it can serve as either the maternal or paternal plant. For many crosses, the outcome is the same regardless of the assigned sex of the parental plants. However, due to increased seed yield and production characteristics, it may be desired to use one parental plant as the maternal plant. Some plants produce tighter ear husks leading to more loss, for example due to rot. There can be delays in silk formation which deleteriously affect timing of the reproductive cycle for a pair of parental inbreds. Seed coat characteristics can be preferable in one plant. Pollen can be shed better by one plant. Other variables can also affect preferred sexual assignment of a particular cross.

The development of a hybrid corn variety involves three steps: (1) selecting plants from various germplasm pools; (2) selfing the selected plants for several generations to produce a series of inbred plants, which although different from each other, each breed true and are highly uniform; and (3) crossing the selected inbred plants with unrelated inbred plants to produce $F_1$ hybrid progeny. During this inbreeding process in corn, the vigor of the plants decreases; however, vigor is restored when two unrelated inbred plants are crossed to produce $F_1$ hybrid progeny. An important consequence of the genetic homozygosity and homogeneity of an inbred plant is that the $F_1$ hybrid progeny of any two inbred varieties are genetically and phenotypically uniform. Plant breeders choose these hybrid populations that display phenotypic uniformity. Once the inbred plants that produce superior hybrid progeny have been identified, the uniform traits of their hybrid progeny can be reproduced indefinitely if the homogeneity of the inbred parents is maintained.

The development of inbred plants generally requires at least about 5 to 7 generations of selfing. Inbred plants are then cross bred to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids. FACT, an acronym for Field Analysis Comparison Trial (strip trials), is an on-farm experimental testing program employed by Monsanto Company to perform the final evaluation of the commercial potential of a product.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and generally are commercially successful. That is, comparisons of experimental hybrids are made to competitive hybrids to determine if there was any advantage to further development of the experimental hybrids. After FACT testing is complete, determinations may be made whether commercial development should proceed for a given hybrid.

The present disclosure provides a genetic complement of the hybrid corn plant variety designated CH010482. As used herein, the phrase "genetic complement" means an aggregate of nucleotide sequences, the expression of which defines the phenotype of a corn plant or a cell or tissue of that plant. By way of example, a corn plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition in which both alleles at a locus are characterized by the same nucleotide sequence or size of a repeated sequence. Heterozygosity refers to different conditions of the gene at a locus. A preferred type of genetic marker is simple sequence repeats (SSRs), although potentially any other type of genetic marker could be used, for example, restriction fragment length polymorphisms (RFLPs), amplified fragment length polymorphisms (AFLPs), single nucleotide polymorphisms (SNPs), and isozymes.

All the compositions and methods disclosed and claimed herein can be made and executed without undue experimentation considering the present disclosure. While the compositions and methods of this disclosure have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the disclosure as defined by the appended claims.

The references cited herein, to the extent that they provide exemplary procedural or other details supplementary to those set forth herein, are specifically incorporated herein by reference.

What is claimed is:

1. A seed of hybrid corn variety CH010482, produced by crossing a first plant of variety CV844363 with a second plant of variety CV957256, wherein representative seeds of said varieties CV844363 and CV957256 are deposited under NCMA Accession No. 202306063 and NCMA Accession No. 202306065, respectively.

2. A plant of the hybrid corn variety CH010482 grown from said seed of claim 1.

3. A plant part of the plant of claim 2, wherein said plant part comprises a cell of said hybrid corn variety CH010482.

4. A composition comprising the seed of claim 1 comprised in plant seed growth media.

5. The composition of claim 4, wherein said growth media is soil or a synthetic cultivation medium.

6. A method of producing the seed of claim 1, the method comprising crossing a plant of variety CV844363 with a plant of variety CV957256.

7. A seed of hybrid corn variety CH010482 further comprising a single locus conversion, wherein a plant grown from said seed comprises a trait conferred by said single locus conversion, and wherein said seed is produced by crossing a first plant selected from the group consisting of variety CV844363 and selfed progeny thereof with a second plant selected from a second group consisting of variety CV957256 and selfed progeny thereof, wherein said first plant, said second plant, or both further comprise said single locus conversion, and wherein representative seeds of said varieties CV844363 and CV957256 are deposited under NCMA Accession No. 202306063 and NCMA Accession No. 202306065, respectively.

8. The seed of claim 7, wherein said single locus conversion confers a trait selected from the group consisting of male sterility, herbicide tolerance, insect resistance, disease resistance, waxy starch, modified fatty acid metabolism, modified phytic acid metabolism, modified carbohydrate metabolism and modified protein metabolism.

9. A plant grown from the seed of claim 7.

10. A method of introducing a heritable trait into hybrid corn variety CH010482, the method comprising the steps of:

(a) introducing at least said heritable trait into a first inbred corn variety CV844363, a second inbred corn variety CV957256, or both inbred corn varieties CV844363 and CV957256 to produce plants of said inbred corn varieties that heritably carry said heritable trait, wherein said heritable trait is introduced into said inbred corn varieties by backcrossing, wherein said backcrossing is sufficient to produce an inbred corn variety further comprising said heritable trait, and wherein representative seeds of said inbred corn varieties CV844363 and CV957256 are deposited under NCMA Accession No. 202306063 and NCMA Accession No. 202306065, respectively; and (b) producing a plant of hybrid corn variety CH010482 further comprising said heritable trait by crossing a plant of said first or said second inbred corn variety that heritably carries said heritable trait with a plant of a different inbred corn variety selected from a group consisting of inbred corn varieties CV844363 and CV957256, or crossing a plant of said first inbred corn variety and a plant of said second inbred corn variety that both heritably carry said heritable trait.

11. The method of claim 10 wherein said heritable trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

12. The method of claim 10 further comprising repeating step (a) at least once to introduce at least a second heritable trait into hybrid corn variety CH010482, wherein the second heritable trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

13. A method of producing a progeny corn plant derived from hybrid corn variety CH010482, wherein the method comprises applying plant breeding techniques to the plant of claim 2 to produce said progeny corn plant derived from hybrid corn variety CH010482.

14. The method of claim 13, wherein said plant breeding techniques comprise backcrossing, marker assisted breeding, pedigree breeding, selfing, outcrossing, haploid production, doubled haploid production, or transformation.

15. The method of claim 13, further comprising the steps of:

(a) crossing said progeny corn plant derived from hybrid corn variety CH010482 with itself or a second plant to produce a seed of a progeny plant of a subsequent generation;

(b) growing the progeny plant of the subsequent generation from said seed of the progeny plant of the subsequent generation; and (c) repeating steps (a) and (b) for at least an additional 3-10 generations to produce a progeny corn plant further derived from the hybrid corn variety CH010482.

16. A method of producing a commodity plant product, the method comprising obtaining the plant of claim 2 or a part thereof and producing said commodity plant product therefrom.

17. The method of claim 16, wherein said commodity plant product is grain, starch, seed oil, corn syrup, or protein.

\* \* \* \* \*